United States Patent [19]
Shine

[11] Patent Number: 5,603,699
[45] Date of Patent: Feb. 18, 1997

[54] NEEDLE GUARD ASSEMBLY

[76] Inventor: Jerry P. Shine, 10451 Isleworth Ave., San Diego, Calif. 92126

[21] Appl. No.: 597,947

[22] Filed: Feb. 7, 1996

[51] Int. Cl.$^6$ ........................................... A61M 5/00
[52] U.S. Cl. ........................ 604/110; 604/192; 604/263
[58] Field of Search .................... 604/110, 187, 604/192, 263

[56] References Cited

U.S. PATENT DOCUMENTS

| | | | |
|---|---|---|---|
| 4,664,259 | 5/1987 | Landis | 604/192 |
| 4,820,277 | 4/1989 | Norelli | 604/192 |
| 5,055,102 | 10/1991 | Sitnik | 604/192 |
| 5,207,653 | 5/1993 | Janjua et al. | 604/192 |

*Primary Examiner*—John D. Yasko
*Attorney, Agent, or Firm*—Deborah A. Dugan

[57] ABSTRACT

In accordance with the present invention, there is provided a needle guard assembly for a hypodermic syringe or other fluid transfer device that offers optimal protection for preventing accidental puncture by a needle after it has been used, maintaining the sterility of a needle prior to use, indicating prior use, preventing reuse, and facilitating safe disposal of a needle after use/injection.

17 Claims, 1 Drawing Sheet

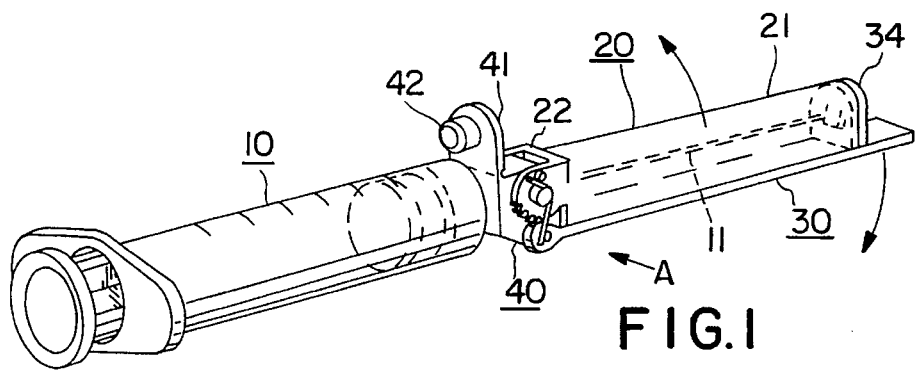
FIG.1
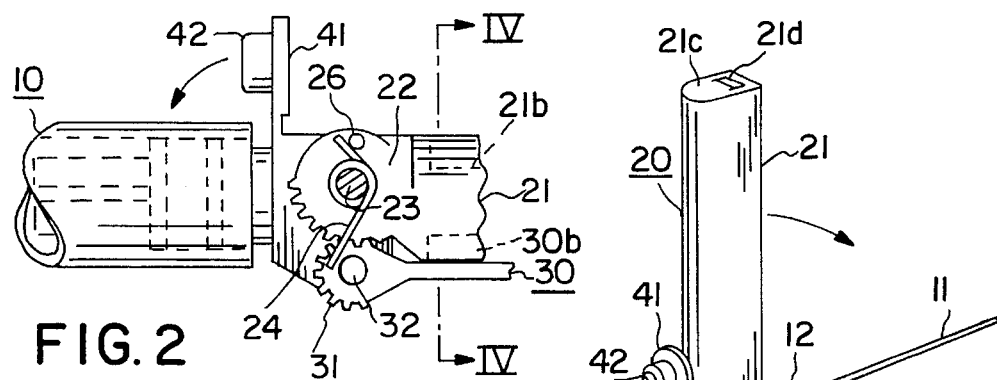
FIG.2   FIG.3
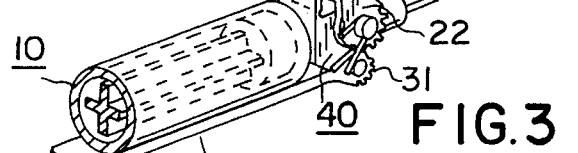
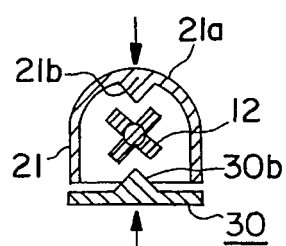
FIG.4
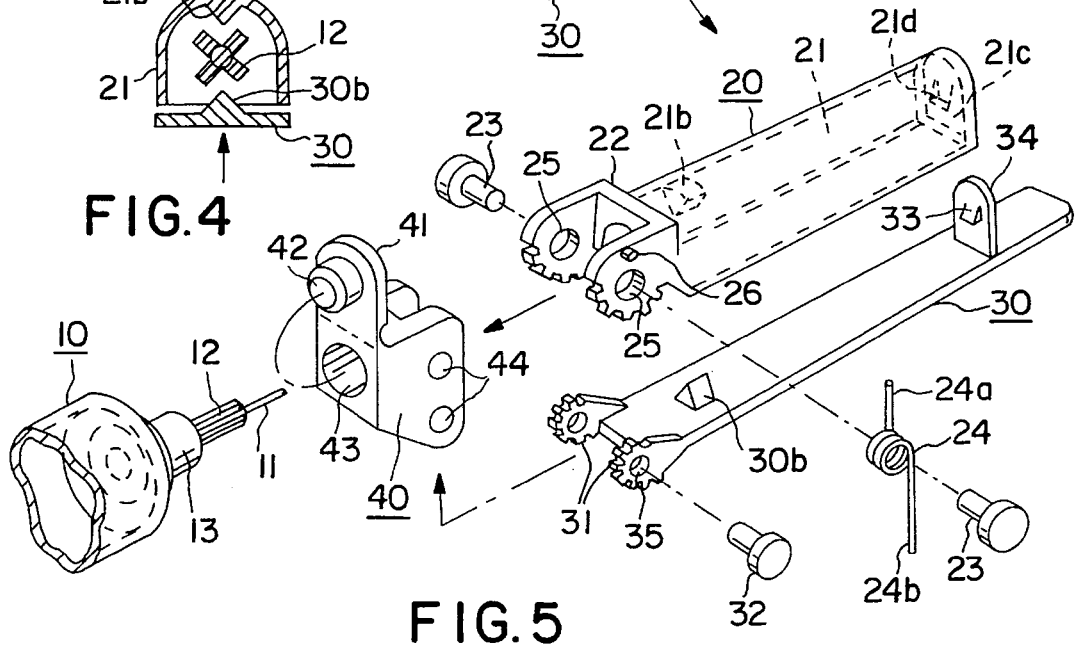
FIG.5

NEEDLE GUARD ASSEMBLY

FIELD OF THE INVENTION

The present invention relates to a protective device for hypodermic syringe needles and the like to prevent accidental puncture by a needle, maintain the sterility of a needle prior to use, indicate prior use of a needle, prevent reuse of a needle, as well as to facilitate safe disposal of a needle after use thereof.

BACKGROUND OF THE INVENTION

The danger of accidental syringe needle puncture has proven a hazard to healthcare professionals since the invention of the syringe. The particular nature of highly toxic medications, for example, radioactive substances, and infectious diseases which have no known cure or are difficult to treat, such as, for example, AIDS and hepatitis, where infection may be transferred via blood, bodily secretions or portions of tissue from the patient to others, particularly via hypodermic syringe needles and the like, creates a serious health risk to patients and healthcare professionals arising from accidental puncture.

A typical hypodermic syringe needle comes with a protective sleeve cover to prevent accidental puncture as well as contamination prior and subsequent to use. In order to use a typical hypodermic syringe the user must manually remove the protective sleeve cover from the needle and manually replace the protective sleeve cover after use/injection. Frequently the protective sleeve cover is not replaced after use. Thus, after the needle is withdrawn from a subject, the tip of the needle is exposed thereby increasing the risk of accidental puncture.

The threat posed by toxic medications and communicable diseases, coupled with an increasing safety awareness amidst the healthcare community and the public, creates an extreme demand for products that protect patients and professionals alike.

Thus, a need exists to develop a device which safely encapsulates and shields a needle tip to prevent accidental puncture and subsequent transfer of toxic material and infectious disease organisms after the needle has been used. The present invention satisfies these needs and provides related advantages as well.

SUMMARY OF THE INVENTION

In accordance with the present invention, there is provided a needle guard assembly for a hypodermic syringe or other fluid transfer device that offers optimal protection for preventing accidental puncture by a needle after it has been used, maintaining the sterility of a needle prior to use, indicating prior use, preventing reuse, and facilitating safe disposal of a needle after use/injection.

The invention provides a protective sheathing for hypodermic syringe needles that can be so formed and produced such that it is an integral member of a hypodermic syringe, an integral member of a removable needle, or an adapter that can be manually attached to commercially available syringes and/or needles.

The invention also provides a safety cover assembly which is adaptable for use with different types of fluid transfer devices, including syringes and tubes, regardless of the specific type of connecting means.

The invention further provides a safety cover assembly which is adaptable for use with needles of varying gauge and length.

The invention also provides a safety cover assembly that remains attached to a hypodermic syringe-needle assembly during deployment of the syringe, but which remains clear of the needle during such deployment.

The invention further provides a safety cover assembly which may be lockingly secured over a contaminated needle to prevent accidental puncture by a needle.

The invention also provides a safety cover assembly which clearly indicates prior use, thereby further preventing unintentional reuse.

The invention additionally provides, for enclosing a needle of a hypodermic syringe, a safety cover assembly which may be safely discarded after use of the needle without significant risk of re-exposing the needle.

Also provided by the subject invention is a remotely-activated protective jacket assembly for a hypodermic syringe needle such that the protective jacket assembly completely encases the needle to ensure sterility of the needle prior to and protection of healthcare personnel and patients after injection.

The subject invention further provides a needle guard assembly mounted on a syringe including a retractable shielding member, a retractable lever member and activating means for enclosing a needle within said assembly.

Further provided by the subject invention is a needle guard assembly that includes a protective jacket assembly which may be activated easily with a single-hand motion away from the needle tip.

BRIEF DESCRIPTION OF THE FIGURES

FIG. 1 is a perspective view showing the needle guard in shielding position as attached to a typical hypodermic syringe.

FIG. 2 is a side view in direction of arrow "A" of FIG. 1 showing the gear engaged hinged mount of the geared shield member clevis and the lever member clevis.

FIG. 3 is a perspective view of the needle guard showing the shield member and the lever member in retracted or open position.

FIG. 4 is a cross-sectional view along line IV—IV of FIG. 2 showing detail of the shield member, needle base spline and lever member.

FIG. 5 is a perspective exploded view showing components of the needle guard assembly.

DETAILED DESCRIPTION OF THE INVENTION

The invention needle guard assembly includes a mounting base block having a bore extending therethrough. The upper end of the bore receives a needle base and the lower end of the bore provides for removable connection to a syringe hub. The upper and lower ends of the bore are shaped and oriented to have a continuous passage therethrough to permit how of a fluid from a needle through the upper end and out through the lower end into a syringe, and/or from a syringe through the lower end into a needle through the upper end.

The jacket assembly of the present invention is pivotally mounted on the mounting base block and comprises a shield member and a lever member.

The needle guard assembly of the present invention further provides activating means adapted for movement of the jacket assembly from a retracted and/or open position wherein a needle is exposed to a closed and/or shielding position wherein a needle is encased within the invention assembly.

The activating means of the present invention comprise a plurality of gears positioned on the jacket assembly.

In a preferred embodiment, invention gears are spur gears having teeth of such form, size and spacing that they mesh with the teeth of additional gears on the needle guard assembly.

The jacket assembly of the invention needle guard comprises a shield member having an open end positioned opposite a closed end and a substantially U-shaped channel extending longitudinally between the open end and the closed end of the shield member. The open end of the shield member forms a U-shaped clevis that is adapted to secure the shield member to the mounting base block as well as to enable pivotal movement of the shield member. As used herein, "clevis" refers to a U-shaped yolk at the end of the shield member or the lever member, between the ends of which a mounting base block can be secured. In a preferred embodiment, the shield member is pivotally mounted to the base block enabling movement from a retracted and/or open position where the needle tip is exposed for injection to a shielding or closed position where the entire needle is enclosed after injection, respectively.

The jacket assembly also comprises a lever member positioned parallel to the shield member on the mounting base block. At one end of the lever member there is formed a U-shaped clevis that is adapted to secure the lever member to the mounting base block and to enable pivotal movement of said lever. The end of the lever member opposite the clevis is free. Proximal to the free end of the lever member is a laterally extending tab shaped and oriented to provide leverage for activating pivotal movement of the jacket assembly.

In a preferred embodiment of the invention, the activating means comprise a first set of gears positioned at the termini of the clevis portion of the shield member that are engaged to a second set of gears positioned at the termini of the clevis portion of the lever member. In a preferred embodiment the first set and second set of gears are shaped and oriented with respect to each other having a gear ratio that enables coordination of movement of said shield member with respect to movement of said lever member. As used herein, "gear ratio" refers to the ratio of rotation of the lever member with respect to the rotation of the shield member.

In one embodiment of the invention, the gear ratio is about 1 to 1. For example, force from a user's finger applied to the laterally extending tab of the lever member is transmitted through invention biasing means to enable about 90 degree movement of said lever member and about 90 degree movement of said shield member, such movement being coordinated to either enclose or expose a needle. In an alternative embodiment, force applied to the laterally extending tab of the lever member is transmitted through invention biasing means to enable about 180 degree movement of the lever member and about 180 degree movement of the shield member wherein the coordinated movement of the lever member and the shield member is disposed toward a needle to enclose or away from a needle to expose the same.

In a preferred embodiment of the invention, the gear ratio is about 2 to 1. For example, force applied to the laterally extending tab of the lever member is transmitted through invention biasing means to enable about 180 degree movement of the lever member and about 90 degree movement of the shield member, whereby the lever member is disposed toward, or alternatively, away from a needle in coordinated movement with the shield member.

Pivotal movement of the shield member and the lever member of the jacket assembly is facilitated by invention biasing means adapted to drive movement of the activating means of the invention needle guard assembly.

Invention biasing means, for example a suitable spring, are adapted for returning the shield member and the lever member into the shielding position when the lever member is released and for activating locking means on the jacket assembly once a needle has been enclosed within.

In a preferred embodiment, invention biasing means comprise a torsion spring pivotally mounted on a first flanged hinge pin. The first flanged hinge pin is adapted for pivotal connection of the shield member to the mounting base. The torsion spring of the present invention comprises a coiled portion and a pair of integrally formed spring arms. The first spring arm is adapted to rest against a second flanged hinge pin. The second flanged hinge pin is adapted for pivotal connection of the lever member to the mounting base block. The second spring arm is adapted to rest against a spring rest prong which is located proximal to the first flanged hinge pin.

In a preferred embodiment, the energy stored in the first spring arm drives rotation of the gears of the lever member and the energy stored in the said second spring arm drives rotation of the gears of the shield member from a retracted or open position to a closed or shielding position around a needle.

The invention needle guard assembly further comprises locking means for securing the shield member to the lever member when the needle guard assembly is in a closed position around a needle. In one embodiment, the locking means comprise a latch member positioned on the laterally extending tab of the lever member and a complementary recess in the closed end of the shield member for receiving and lockingly engaging the jacket assembly of the invention around a needle. Invention locking means enable secure enclosure of the needle by the combination of the shield member and the lever member.

Deployment of the invention needle guard assembly is initiated upon the exertion of a force or pressure on the tab portion of the lever member by, for example, a user's finger. Such force is transmitted through biasing means which drive the coordinated rotation of the spur gears positioned on the clevis portion of the lever member which, in turn, mesh with and rotate the spur gears of the shield member.

Further provided by the invention assembly are disengagement means for removing a needle enclosed in the jacket assembly from a syringe. In one embodiment, the disengagement means comprise at least one inwardly projecting tooth on the U-shaped channel portion of the shield member positioned proximal to the open end thereof and at least one inwardly projecting tooth on the lever member positioned proximal to the clevis portion thereof. In a preferred embodiment, the teeth are grip teeth, being shaped and oriented to align with a spline on a base of a syringe needle allowing a user to unscrew and to remove the needle from the syringe hub. The grip teeth facilitate engagement of the invention assembly with a splined needle base such that by compressing the base portions of the shield member and lever member, for example, with thumb and forefinger, the teeth engage the spline(s) of the needle base and rotation of either the needle guard assembly or the syringe cause disengagement of the needle guard assembly and the needle encased therein from a syringe.

The invention needle guard assembly includes sealing means for closing the opening at the base of a needle after the needle, encased in the needle guard assembly has been removed from a syringe. In a preferred embodiment, invention sealing means comprise an integrally formed plug member that extends laterally from the guard mounting base block of the needle guard assembly. The plug member can be used to seal the opening at the base of a needle once the needle guard assembly has been removed from the syringe hub, thereby, completely encapsulating the needle for safe disposal.

In a preferred embodiment, the invention assembly is flexible, for example, one made of plastic, and can either be attached at the time the hypodermic syringe, needle, or other fluid transfer device is manufactured or, alternatively the invention assembly can be supplied separately as a modular component and mounted when needed. Suitable materials for the invention assembly may be plastic, glass, and/or metal.

The benefits of the invention assembly include ease of use, single-handed operation, simplicity, adaptability of the basic design to different needle sizes and attachment means types, sterile enclosure, prior use indication, reuse prevention, safe disposal, and prevention of accidental needle puncture.

Preferred embodiments of the invention are illustrated in the accompanying drawings.

As shown in FIG. 1, the present invention provides a needle guard assembly -20 attached to a typical hypodermic syringe -10. The needle guard assembly having a substantially U-shaped shield member -21 is hingeably attached and gear-engaged to a lever member -30. The shield member -21 and the lever member -30 are pivotally mounted on a guard mounting base block -40. Extending laterally from the guard mounting base block -40 is a syringe mounting bore closure means -41 integrally hinged thereto. The needle guard assembly in mode shown completely encloses the syringe needle -11.

As shown in FIG. 2 and FIG. 5, there is provided a substantially U-shaped shield member -21 having a spur-geared clevis portion -22 pivotally mounted by a first set of flanged hinge pins -23 to the guard mounting base block -40. A lever member -30 is also pivotally mounted to the guard mounting base block -40 by a second set of flanged hinge pins -32 (only one pin shown). The spur gears of the lever member are designed to mesh with the spur gears of the shield member -22. The gear ratio of the lever member gears and the shield member gears enables coordinated movement of the jacket assembly of the invention needle guard assembly.

In one embodiment of the invention, the gear ratio is about 1 to 1 to provide about 90 degree movement of the lever member -30 and about 90 degree movement of the shield member -21.

In an alternative embodiment, the 1 to 1 gear ratio provides about 180 degree movement of the lever member -30 and about 180 degree movement of the shield member -21.

As shown in FIG. 3, in a more preferred embodiment the gear ratio is about 2 to 1 to provide about 180 degree movement of the lever member -30 and about 90 degree movement of the shield member -21. As illustrated, the shield member -21 is shown retracted by action of geared motion through finger pressure onto the lever member -30 all toward the syringe body -10 exposing the syringe needle -11 for injection mode.

A torsional coil spring -24 is mounted to a first flanged hinge pin -23 of the shield member -21 and is positioned by a spring prong -24 for a first spring arm -24a and a second flanged hinge pin -32 of the lever member for a second spring arm -24b. The spring force provides instant return of the shield member -21 and lever member -30 to encase the needle when released after injection mode.

As shown in FIG. 4, the substantially U-shaped channel portion -22 of the shield member -21 is provided with a triangular-shaped, downward protruding grip tooth -21b. The upper surface -30a of the lever member -30 is also provided with a triangular-shaped protruding grip tooth -30b. By exerting force upon and/or compressing a flexible portion -21a of the shield member -21 portion and compressing the lever member -30 at the location of tooth -30b, the teeth -30b and -21b engage the splined needle base -12 screwed into the syringe hub portion -13c to provide gripping means to unscrew and to remove the covered needle from the syringe hub by rotating the needle guard assembly or the syringe.

As shown in FIG. 5, the needle guard assembly -20 is comprised of a mounting base block -40 having an integrated hinged closure latch -41 with a plug -42 to close and/or seal the syringe bore -43 when the needle is removed from the syringe and stored within the guard assembly for disposal.

The mounting base block includes a first bore -43 for attachment of the invention assembly -20 to the syringe -10, and at least two parallel bores -44 to each side thereof enabling press-it of hinge pins -23 and -32.

The substantially U-shaped shield member -21 includes a geared clevis portion -22 having a set of parallel bores -25 for receiving hinge pins -23 and a spring rest prong -26.

The closed end of the shield -21c is provided with a lock recess -21d for engagement with a lock clip -33 of the laterally extending tab -34 of the lever member -30.

The lever member -30 comprises a geared clevis portion -31 having a set of parallel bores -35 for flanged hinge pins -32 and a triangular-shaped tooth -30b protruding from the upper surface of the lever.

Although the invention has been described with reference to the disclosed embodiments, those skilled in the art will readily appreciate that the specific embodiments described hereinabove are only illustrative of the invention. It should be understood that various modifications can be made without departing from the spirit of the invention. Accordingly, the invention is limited only by the following claims.

What is claimed is:

1. A needle guard assembly comprising:
   a mounting base having a bore extending therethrough, said bore having an upper end for receiving a needle base and a lower end for removable connection to a syringe hub, said upper and lower ends being shaped and oriented to have a continuous passage therethrough designed permit flow of a fluid from a needle through the upper end and out through the lower end into a syringe, and from a syringe through the lower end into a needle through the upper end:
   a jacket assembly pivotally mounted on said mounting base comprising:
   i.) a shield member having an open end positioned opposite a closed end, said open end terminating in a U-shaped clevis portion adapted to enable pivotal movement of said shield, and having a substantially U-shaped channel extending longitudinally between said open end and said closed end; and ii.) a lever member positioned on said base parallel to said shield member having at one end a U-shaped clevis portion adapted to enable pivotal movement of said lever positioned opposite a free end and a laterally extending tab proximal to said free end thereof, wherein said tab is shaped and oriented to provide leverage for initiating pivotal movement of said lever from a retracted position and to align with and engage said closed end of said shield when said needle guard assembly is in a closed position around a needle;

activating means adapted for movement of the jacket assembly from a retracted position to a closed position; and biasing means adapted to drive movement of the activating means.

2. The needle guard assembly of claim 1 wherein the activating means comprise a plurality of gears positioned on the jacket assembly.

3. The needle guard assembly of claim 2 wherein the activating means comprise a first set of gears positioned at the termini of the clevis portion of said shield member and a second set of gears positioned at the termini of the clevis portion of said lever member.

4. The needle guard assembly of claim 3 wherein the first set of gears are spur gears having teeth of such form, size and spacing that they mesh with the teeth of a second set of spur gears on the clevis portion of the lever member.

5. The needle guard assembly of claim 1 wherein the biasing means comprise a torsion spring pivotally mounted on a first flanged hinge pin, said first pin adapted for pivotal connection of said shield member to said mounting base, said torsion spring comprising a coiled portion and a pair of integrally formed spring arms, said spring arms comprising a first spring arm adapted to rest against a second flanged hinge pin, said second pin adapted for pivotal connection of said lever member to said mounting base, and a second spring arm adapted to rest against a spring rest prong proximal to said first flange pin.

6. The needle guard assembly of claim 5 wherein the energy stored in said spring arms drives rotation of the gears of said lever member and said shield member the energy stored in said second spring arm drives rotation of the gears of said shield member from a retracted position to a closed position around a needle.

7. The needle guard assembly of claim 3 having a gear ratio that enables coordination of movement of said shield member with respect to movement of said lever member.

8. The needle guard assembly of claim 7 wherein the gear ratio is about 1 to 1.

9. The needle guard assembly of claim 8 wherein force applied to the laterally extending tab of the lever member is transmitted through said biasing means to enable about 90 degree movement of said lever member and about 90 degree movement of said shield member whereby said lever member is disposed toward a needle in coordinated movement with said shield member.

10. The needle guard assembly of claim 8 wherein force applied to the laterally extending tab of the lever member is transmitted through said biasing means to enable about 180 degree movement of said lever member and about 180 degree movement of said shield member whereby said lever member is disposed toward a needle in coordinated movement with said shield member.

11. The needle guard assembly of claim 7 wherein the gear ratio is about 2 to 1.

12. The needle guard assembly of claim 11 wherein force applied to the laterally extending tab of the lever member is transmitted through said biasing means to enable about 180 degree movement of said lever member and about 90 degree movement of said shield member whereby said lever member is disposed toward a needle in coordinated movement with said shield member.

13. The needle guard assembly of claim 1 wherein the jacket assembly further comprises locking means for securing the shield member to the lever member when the needle guard assembly is in a closed position.

14. The needle guard assembly of claim 13 wherein the locking means comprise a latch member positioned on the laterally extending tab of said lever member and a complementary recess in the closed end of said shield member for receiving and lockingly engaging said jacket assembly around a needle.

15. The needle guard assembly of claim 1 wherein the jacket assembly further comprises disengagement means for removing a needle enclosed in said jacket assembly from a syringe.

16. The needle guard assembly of claim 15 wherein the disengagement means comprise at least one inwardly projecting tooth on said channel portion of said shield member proximal to said open end and at least one inwardly projecting tooth on said lever member proximal to said clevis portion, said tooth being shaped and oriented to align with a spline on a base of a syringe needle, such that upon exertion of force upon said tooth the spline is engaged thereby, whereupon rotation of said jacket assembly disengages the guard assembly and needle encased therein from a syringe.

17. The needle guard assembly of claim 1 wherein the mounting base further comprises sealing means for closing the opening at the base of a needle after the needle, encased in said needle guard assembly has been removed from said syringe.

* * * * *